US006448059B1

(12) United States Patent
Hou (10) Patent No.: US 6,448,059 B1
(45) Date of Patent: Sep. 10, 2002

(54) METHODS AND COMPOSITION FOR INHIBITION OF TRNA ACTIVITIES (75) Inventor: Ya-Ming Hou, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/506,768

(22) Filed: Feb. 18, 2000

Related U.S. Application Data (63) Continuation-in-part of application No. 08/928,362, filed on Sep. 12, 1997, now abandoned.
(60) Provisional application No. 60/026,094, filed on Sep. 13, 1996.

(51) Int. Cl.[7] ............................. C12N 1/00; C12N 1/20; C12Q 1/68; C12P 19/34; C07H 21/04
(52) U.S. Cl. ...................... 435/243; 435/252.33; 435/6; 435/91.1; 536/23.1; 536/24.3; 536/24.31; 536/24.33; 536/24.32; 536/24.5
(58) Field of Search ........................... 435/6, 91.1, 440, 435/183, 325, 375, 243, 252.33, 320.1; 514/44; 536/23.1, 24.3, 24.32, 24.33, 24.5

(56) References Cited

U.S. PATENT DOCUMENTS 5,821,052 A  * 10/1998 Chen et al.

OTHER PUBLICATIONS

Branch, A.D. TIBS, vol. 23, Feb. 1998, pp. 45–50.*
Jen et al., Stem Cells 2000; 18:307–319.*
Green et al., J. A. Coll. Surg., (Jul. 2000).*
Hou et al., PNAS 90, pp. 6776–6780 (1993).*

* cited by examiner

Primary Examiner—Andrew Wang
Assistant Examiner—Karen A Lacourciere
(74) Attorney, Agent, or Firm—William J. McNichol, Jr.; Nanda P. B. A. Kumar (57) ABSTRACT A method of inhibiting activities of a tRNA of a selected pathogen is provided wherein a cell infected with a selected pathogen is contacted with an effective amount of an oligonucleotide targeted to a region of the cloverleaf structure of a tRNA of the selected pathogen. Compositions for inhibiting activities of a tRNA of a selected pathogen which contain an oligonucleotide targeted to a region of cloverleaf structure of a tRNA of the selected pathogen are also provided. In addition, methods of killing the pathogen with these compositions are provided.

24 Claims, 2 Drawing Sheets

SEQUENCE LISTING

<160> NUMBER OF SEQ ID NOS: 15

<210> SEQ ID NO 1
<211> LENGTH: 18
<212> TYPE: RNA
<213> ORGANISM: Artificial Sequence
<220> FEATURE:
<223> OTHER INFORMATION: E. coli D stem-loop

<400> SEQUENCE: 1
uaacaaagcg guuaugua                                                         18

<210> SEQ ID NO 2
<211> LENGTH: 18
<212> TYPE: RNA
<213> ORGANISM: Artificial Sequence
<220> FEATURE:
<223> OTHER INFORMATION: Yeast D stem-loop

<400> SEQUENCE: 2
uggcgcagug guagcgca                                                         18

<210> SEQ ID NO 3
<211> LENGTH: 18
<212> TYPE: RNA
<213> ORGANISM: Artificial Sequence
<220> FEATURE:
<223> OTHER INFORMATION: E. coli D stem-loop

<400> SEQUENCE: 3
uaacauaccg guaaugua                                                         18

<210> SEQ ID NO 4
<211> LENGTH: 14
<212> TYPE: RNA
<213> ORGANISM: Artificial Sequence
<220> FEATURE:
<223> OTHER INFORMATION: E. coli D stem-loop

<400> SEQUENCE: 4
acaaagcggu uaug                                                             14

<210> SEQ ID NO 5
<211> LENGTH: 10
<212> TYPE: RNA
<213> ORGANISM: Artificial Sequence
<220> FEATURE:
<223> OTHER INFORMATION: E. coli D stem-loop

<400> SEQUENCE: 5
aaagcgguua                                                                  10

<210> SEQ ID NO 6
<211> LENGTH: 10
<212> TYPE: RNA
<213> ORGANISM: Artificial Sequence
<220> FEATURE:
<223> OTHER INFORMATION: E. coli D stem-loop

<400> SEQUENCE: 6
aagcgguuau                                                                  10

<210> SEQ ID NO 7
<211> LENGTH: 5

-continued

```
<212> TYPE: RNA
<213> ORGANISM: Artificial Sequence
<220> FEATURE:
<223> OTHER INFORMATION: E. coli D stem-loop

<400> SEQUENCE: 7 aagcg                                                                      5

<210> SEQ ID NO 8
<211> LENGTH: 8
<212> TYPE: RNA
<213> ORGANISM: Artificial Sequence
<220> FEATURE:
<223> OTHER INFORMATION: E. coli acceptor stem

<400> SEQUENCE: 8 cgccucca                                                                   8

<210> SEQ ID NO 9
<211> LENGTH: 10
<212> TYPE: RNA
<213> ORGANISM: Artificial Sequence
<220> FEATURE:
<223> OTHER INFORMATION: E. coli acceptor stem-loop

<400> SEQUENCE: 9
aauccgucua                                                                10

<210> SEQ ID NO 10
<211> LENGTH: 13
<212> TYPE: RNA
<213> ORGANISM: Artificial Sequence
<220> FEATURE:
<223> OTHER INFORMATION: E. coli T(C Stem-loop

<400> SEQUENCE: 10
cgguucgaca ccg                                                            13

<210> SEQ ID NO 11
<211> LENGTH: 74
<212> TYPE: RNA
<213> ORGANISM: Escherichia coli

<400> SEQUENCE: 11
ggcgcguuaa caaagcgguu auguagcgga uugcaaaucc gucuaguccg guucgacucc          60
ggaacgcgcc ucca                                                           74

<210> SEQ ID NO 12
<211> LENGTH: 74
<212> TYPE: RNA
<213> ORGANISM: Haemophilus influenzae

<400> SEQUENCE: 12
ggcguguuag caaagcgguu augcacugga uugcaaaucc auguagcucg guucgacucc          60
gggacacgcc ucca                                                           74

<210> SEQ ID NO 13
<211> LENGTH: 34
<212> TYPE: DNA
<213> ORGANISM: Artificial Sequence
<220> FEATURE:
<223> OTHER INFORMATION: Primer

<400> SEQUENCE: 13
```

-continued

```
gcggtcgaca tgctaaaaat tttcaataccttaa                                      34

<210> SEQ ID NO 14
<211> LENGTH: 34
<212> TYPE: DNA
<213> ORGANISM: Artificial Sequence
<220> FEATURE:
<223> OTHER INFORMATION: Primer

<400> SEQUENCE: 14
cgcactagtc tattgcttac gccaagttgt ccca                                     34

<210> SEQ ID NO 15
<211> LENGTH: 16
<212> TYPE: PRT
<213> ORGANISM: Artificial Sequence
<220> FEATURE:
<223> OTHER INFORMATION: N-terminal (His)6 tag

<400> SEQUENCE: 15

Met Arg Gly Ser His His His His His His Ser Ser Gly Trp Val Asp
1               5                   10                  15
```

METHODS AND COMPOSITION FOR INHIBITION OF TRNA ACTIVITIES

This application is a continuation-in-part of U.S. application Ser. No. 08/928,362, filed Sep. 12, 1997, now abandoned which claims the benefit of U.S. Provisional Application No. 60/026,094, filed on Sep. 13, 1996.

BACKGROUND OF THE INVENTION

Aminoacylation of tRNAs by their cognate aminoacyl tRNA synthetases is fundamental to protein synthesis. This reaction attaches an amino acid to the 3' end of a tRNA so that the amino acid can be delivered to the growing polypeptide chain as the anticodon sequence of the tRNA reads a codon triplet in a mRNA. The specificity of aminoacylation is determined by the ability of an aminoacyl tRNA synthetase to interact with the correct amino acid and to recognize its cognate tRNA through specific nucleotides (Schimmel, P. & Söll, D. (1979) Ann. Rev. Biochem. 48, 601–648; Meinnel et al. (1995) in tRNA: Structure, biosynthesis, and function, Söll, D. & RajBhandary, U., eds, pages 251–292, American Society for Microbiology, Washington, DC). Interference with either the amino acid binding step or the tRNA recognition step of a synthetase can inhibit aminoacylation and arrest protein synthesis, thereby leading to cell death. tRNA also functions as a primer for reverse transcriptase by viral polymerase during the replication cycle of retroviruses.

Several amino acid analogs have proven useful as inhibitors of aminoacylation (Aldridge, K. E. (1992) Antimicrobial Agents and Chemotherapy 36, 851–853; Yanagisawa et al. (1994) J. Biol. Chem. 269, 24303–24309). However, these analogs are not targeted at the tRNA recognition step.

Recent studies have shown that the specific nucleotides important for tRNA recognition can vary from one organism to another (Sampson et al. (1989) Science 243, 1363–1366; Nazarenko et al. (1992) Nucleic Acids Res. 20, 475–478). The species-specific nucleotides account for the species-selective aminoacylation of tRNA acceptor stems by the cognate synthetases (Hipps et al. (1995) Proc. Natl. Acad. Sci. USA 92, 5550–5552; Hou et al. (1995) RNA 1, 707–713; Quinn et al. (1995) Biochemistry 34, 12489–12495). Substitutions of these nucleotides reduce aminoacylation while transfer of these nucleotides to the analogous positions of a heterologous tRNA (tRNA from a different organism) confer recognition and aminoacylation of that tRNA by the heterologous synthetase.

However, targeting specific nucleotides of tRNAs has proven difficult. Previous studies demonstrated that the secondary cloverleaf structure of tRNAs and its L shaped tertiary structure limited the accessibility of complementary oligoribonucleotides to specific regions (Uhlenbeck, O. C. (1972) J. Mol. Biol. 65, 25–41; Schimmel et al., (1972) Biochemistry 11, 642–646; Freier, S. M. & Tinoco, I. (1975) Biochemistry 14, 3310–3314) These accessible regions include the NCCA sequence at the 3' end, the anticodon loop, a portion of the D loop, and a portion of the variable loop. None of the nucleotides in the stem regions were accessible to oligoribonucleotides. In those early studies, oligoribonucleotides of 3–4 residues in length were used. In a more recent study, a 13-mer oligoribonucleotide was used to probe the anticodon loop of E. coli tRNAfMet (Hayase et al. (1990) Biochemistry 29, 8793–8797). However, due to the unusual conformation of the anticodon loop, the 13-mer did not gain access to the tRNA until the higher order tRNA structure was melted first.

It has now been found that modified oligonucleotides can target species-specific tRNA nucleotides and provide a basis for drug design for inhibition of activities of a tRNA from one organism but not from others. In the present invention, oligonucleotide sequences which bind to the critical nucleotides in a tRNA that are recognized by the cognate aminoacyl tRNA synthetase are provided. Such oligonucleotides are useful as antibiotics, inhibiting aminoacylation of a tRNA of a selected pathogen and thereby killing the pathogen. Using the methods of the present invention, oligonucleotides which inhibit other activities of pathogenic tRNA can also be designed.

SUMMARY OF THE INVENTION

An object of the present invention is to provide a method of inhibiting activities of a tRNA of a selected pathogen comprising contacting a cell infected with the selected pathogen with an effective amount of an oligonucleotide targeted to a region of a cloverleaf structure of the tRNA of the selected pathogen.

Another object of the present invention is to provide compositions capable of inhibiting activity of a tRNA of a selected pathogen comprising an oligonucleotide targeted to a region of a cloverleaf structure of the tRNA of the selected pathogen.

BRIEF DESCRIPTION OF THE FIGURES

FIG. 1 shows the sequence and cloverleaf structure of E. coli tRNA$^{Cys}$ SEQ ID NO:11. U73, G15:G48, and the GCA anticodon are shaded to indicate that they are the major nucleotide determinants for recognition by cysteine tRNA synthetase. Nucleotides are numbered based on the system established for yeast tRNA$^{Phe}$ by Steinberg et al. (1993) Nucleic Acids Res. 21, 3011–3015 such that A14, G15, G18, and G19 are preserved while nucleotide 17 is missing in the D loop. Thin lines indicate tertiary hydrogen bonds that stabilize the L-shaped tRNA tertiary structure.

FIG. 2 shows the sequence and cloverleaf structure of H. influenzae tRNA$^{Cys}$ SEQ ID NO:12. As in FIG. 1, U73, G15:G48, and the GCA anticodon are shaded to indicate that they are the major nucleotide determinants for recognition by cysteine tRNA synthetase. Nucleotides are numbered based on the system established for yeast tRNA$^{Phe}$ by Steinberg et al. (1993) Nucleic Acids Res. 21, 3011–3015 such that A14, G15, G18 and G19 are preserved while nucleotide 17 is missing in the D loop. Thin lines indicate tertiary hydrogen bonds that stabilize the L-shaped tRNA tertiary structure.

DETAILED DESCRIPTION OF THE INVENTION

The present invention provides methods of inhibiting the activity of a pathogenic tRNA using oligonucleotide sequences targeted to species-specific nucleotides in the highly structured cloverleaf region of a tRNA of the pathogen so that the oligonucleotide sequence will only bind to the pathogenic tRNA and not to the host tRNA. By "activity" of a pathogenic tRNA it is meant to include, but is not limited to, known activities such as aminoacylation, peptide bound formation in protein synthesis, and serving as a primer for reverse transcriptase during the replication cycle of retroviruses. By inhibiting an activity such as aminoacylation of a selected pathogenic tRNA, the oligonucleotides act as antibiotics, capable of killing the infectious organisms. By "pathogen" it is meant to include any organism causing disease such as, but not limited to, viruses, bacteria, fungi, yeasts and protozoans. Because the method and compounds target a highly structured cloverleaf region of the tRNA which is conserved in evolution, it is unlikely that all of the nucleotides that contribute to this cloverleaf structure would mutate simultaneously. Thus, this structured region provides a more stable target for antibiotics than individual nucleotides. The current crisis of antibiotic resistance of pathogens arises in part from target site mutations. Accordingly, the present method is especially useful in designing oligonucleotide sequences that are effective against pathogens having such point mutations.

In this method, a cell infected with the pathogen is contacted with an effective amount oligonucleotide targeted to a region of a cloverleaf structure of the tRNA of the pathogen. By "effective amount" it is meant a concentration of an oligonucleotide which binds to the tRNA and causes inhibition of an activity of tRNA, i.e., aminoacylation or peptide bound formation in protein synthesis. Such concentrations can be routinely determined by those skilled in the art in accordance with procedures disclosed herein.

The present invention further relates to compositions capable of inhibiting activities of a tRNA of a selected pathogen which comprise an oligonucleotide targeted to a region of a cloverleaf structure of a tRNA of the selected pathogen. In a preferred embodiment, the oligonucleotides are 2'-O-alkyl oligonucleotides since these modified oligonucleotides have been demonstrated to be completely resistant to degradation by either RNA or DNA specific nucleases (Sproat et al., (1989) *Nucleic Acids Res.* 17, 3373–3386 1993). However, other modifications which increase the resistance of oligonucleotides to RNA or DNA specific nucleases can also be incorporated into the oligonucleotides. Such modifications are well known to those of skill in the art. Compositions of the present invention may also comprise a suitable delivery vehicle. The determination of a suitable vehicle will be dependent upon the mode of delivery and the host to which the composition is being administered to. Determination of a suitable vehicle is performed routinely by those of skill in the art.

The oligonucleotides of the present invention also serve as a model for the design of antibiotics which specifically target the tRNA of infectious pathogens. Structural analysis of the tRNA-oligonucleotide complexes to elucidate their three dimensional structure will facilitate the development of antibiotics that are potent, specific, and can be delivered successfully to a pathogen.

A series of oligonucleotides complementary to the major nucleotide determinants for aminoacylation of *E. coli* tRNA$^{Cys}$ were synthesized. U73 and the GCA anticodon of *E. coli* tRNA$^{Cys}$ have been determined to be nucleotide determinants for aminoacylation (Pallanck et al. (1992) *J. Biol. Chem.* 267, 7221–7223; Hou et al. (1993) *Proc. Natl. Acad. Sci. USA* 90, 6776–6780; Komatsoulis, G. A. & Abelson, J. (1993) *Biochemistry* 32, 7435–7444). In addition, a G15:G48 tertiary hydrogen base pair that connects the dihydrouridine (D) loop with the variable loop has been shown to be an important structural determinant that contributes to aminoacylation (Hou et al., (1993) *Proc. Natl. Acad. Sci. USA* 90, 6776–6780; Hou, Y. M. (1994) *Biochemistry* 33, 4677–4681). Substitution of G15:G48 with G15:C48 reduces the catalytic efficiency of aminoacylation by 2 orders of magnitude (Hou et al., (1993) *Proc. Natl. Acad. Sci. USA* 90, 6776–6780). Inspection of available tRNA genes and sequences for cysteine tRNAs shows that U73 and the GCA anticodon are conserved in evolution. In contrast, while *B. subtilis*, yeast, mouse and human all have a G15:C48 base pair, organisms such as *E. coli* (Steinberg et al. (1993) *Nucleic Acids Res.* 21, 3011–3015) and *H. influenzae* have G15:G48. Aminoacylation of yeast tRNA$^{Cys}$ by the *E. coli* cysteine enzyme has a catalytic efficiency 2 orders of magnitude below that of *E. coli* tRNA$^{Cys}$ (Hou et al. (1995) *RNA* 1, 707–713). Although yeast tRNA$^{Cys}$ differs from *E. coli* tRNA$^{Cys}$ in many more nucleotides than just the G15:G48 base pair, the identical catalytic efficiency of aminoacylation of yeast tRNA$^{Cys}$ and of the G15:C48 variant of *E. coli* tRNA$^{Cys}$ suggests a kinetic parallel between the two tRNAs. It is believed that the requirement for the G15:G48 tertiary base pair of *E. coli* tRNA$^{Cys}$ accounts for the species-specific aminoacylation against yeast tRNA$^{Cys}$ by the *E. coli* cysteine tRNA synthetase.

The G15:G48 tertiary base pair of *E. coli* tRNA$^{Cys}$ is capable of forming 2 hydrogen bonds through the unusual N2 and N3 positions of the purine ring (Hou et al., (1993) *Proc. Natl. Acad. Sci. USA* 90, 6776–6780). The G15:G48 tertiary base pair is located within the core structure of tRNA$^{Cys}$, which consists of multiple tertiary hydrogen and stacking interactions in the D and TψC loops. Despite this location within the core structure, it has now been demonstrated that a 2'-O-methyl (2'-O—Me) oligonucleotide complementary to an 18-base long sequence which includes G15 stably binds to *E. coli* tRNA$^{Cys}$ and discriminates against yeast tRNA$^{Cys}$. Additional experiments show that 2'-O—Me oligonucleotides as short as a 10-mer can bind to G15 and its surrounding sequences of *E. coli* tRNA$^{Cys}$. The stoichiometric binding of the 10-mer to the tRNA completely inhibits aminoacylation. Because the 10-mer dissociates from *E. coli* tRNA$^{Cys}$ significantly slower than that of cysteine tRNA synthetase, it is an effective competitor against the enzyme for tRNA$^{Cys}$. This 10-mer, within the statistical boundaries that define unique RNA sequences in bacteria, provides an example of sequence specific inhibitor of tRNA aminoacylation.

Table 1 provides a list of synthesized oligonucleotide sequences that target *E. coli* and yeast tRNA$^{Cys}$.

TABLE 1

2'-O—Me oligonucleotides that target *E. coli* and yeast tRNA$^{CYS}$

| SEQ ID NO | Targeted Sequence and Structure |
| --- | --- |
| 01 | 5'-U$^8$AACAAAGCGGUUAUGUA$^{26}$-3' (*E. coli* D stem-loop) |
| 02 | 5'-U$^8$GGCGCAGUGGUAGCGCA$^{26}$-3' (yeast D stem-loop) |
| 03 | 5'-U$^8$AACAUACCGGUAAUGUA$^{26}$-3' (*E. coli* D stem-loop) |
| 04 | 5'-A$^{10}$CAAAGCGGUUAUG$^{24}$-3' (*E. coli* D stem-loop) |
| 05 | 5'-A$^{12}$AAGCGGUUA$^{22}$-3' (*E. coli* D stem-loop) |
| 06 | 5'-A$^{13}$AGCGGUUAU$^{21}$-3' (*E. coli* D loop) |
| 07 | 5'-A$^{13}$AGCG$^{18}$-3' (*E. coli* D loop) |
| 08 | 5'-C$^{69}$GCCUCCA$^{76}$-3' (*E. coli* Acceptor stem) |
| 09 | 5'-A$^{37}$AUCCGUCUA$^{46}$-3' (*E. coli* AC stem-loop) |
| 10 | 5'-C$^{51}$GGUUCGACACCG$^{64}$-3 (*E. coli* TψC stem-loop) |

Each oligonucleotide sequence of Table 1 was synthesized with uniform 2'-O—Me substitutions and a 3' terminal acridine. These modifications have been shown to increase affinity for complementary RNA compared to unmodified DNA oligonucleotides (Asseline et al. (1984) *Proc. Natl. Acad. Sci.* 81, 3297–3301; Inoue et al. (1987) *Nucleic Acid*

Res. 15, 6131–6148, 1987; Sproat, B. S. & Lamond, A. I. (1993) in *Antisense Research and Application*, Crooke, S. T. & LeBleu, B., eds, pages 351–362, CRC Press, Boca Raton, Fla). These oligonucleotides were then tested to determine their efficacy as inhibitors that bind to *E. coli* tRNA$^{Cys}$ in its native structure and inhibit the ability of the tRNA to be aminoacylated by the cognate cysteine tRNA synthetase.

Figure 1:
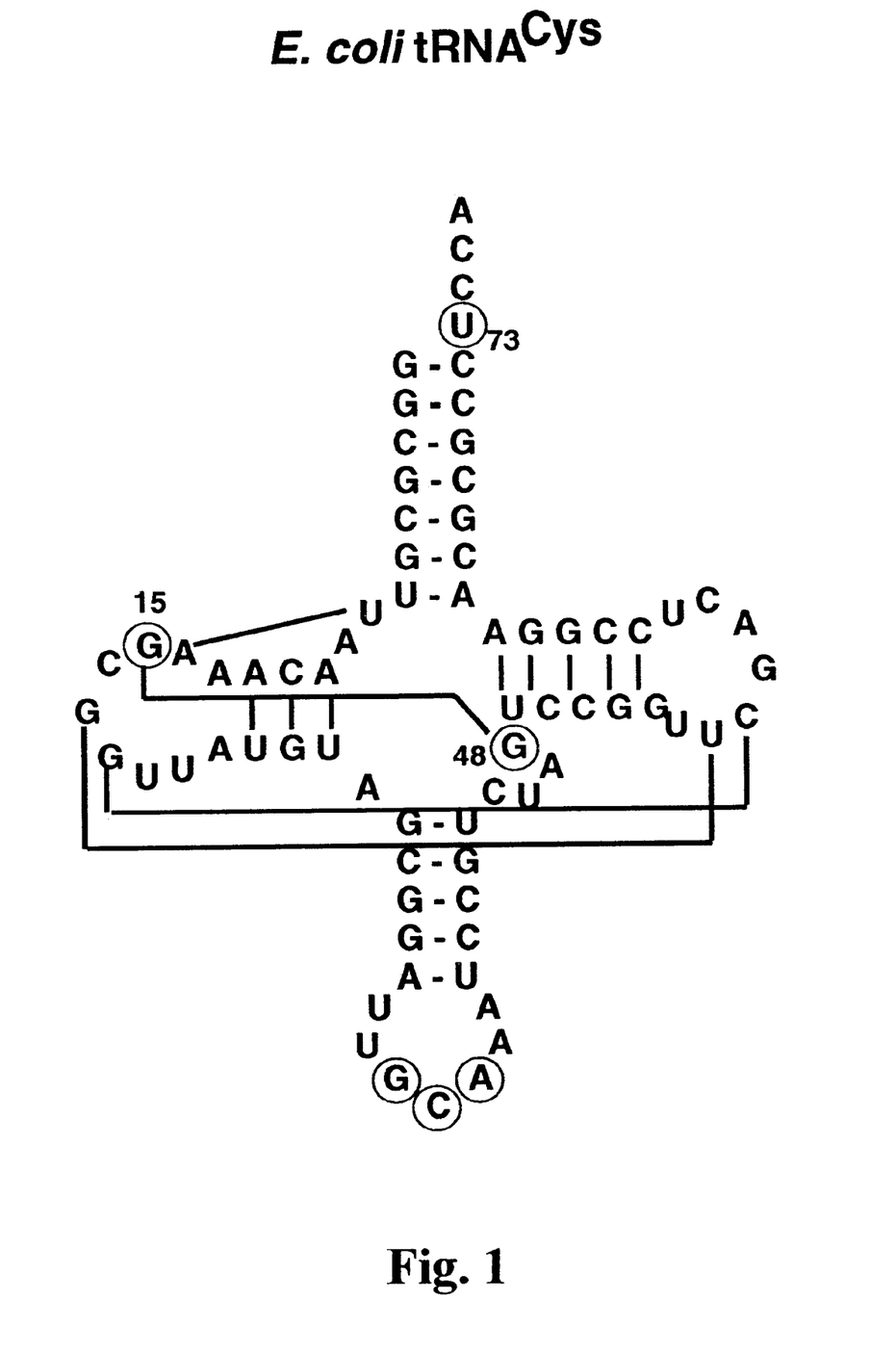

Based on the sequence of *E. coli* tRNA$^{Cys}$ (FIG. 1), oligonucleotide 01 which is complementary to the sequence from U8 to A26 in the D stem-loop of the tRNA was synthesized. The target sequence consists of 18 nucleotides and includes the critical G15. Except for C16 and U20, every nucleotide in the target is involved in a Watson-Crick or tertiary hydrogen base pair or base triple. At a ratio of 6 $\mu$M:3 $\mu$M of oligonucleotide 01 to tRNA, oligonucleotide 01 formed a stable complex with *E. coli* tRNA$^{Cys}$ in a gel shift assay. To form this complex, a previously denatured and properly reannealed T7 transcript of *E. coli* tRNA$^{Cys}$ was incubated with the oligonucleotide. Prior to the addition of the oligonucleotide, the pre-annealed tRNA$^{Cys}$ was an efficient substrate for *E. coli* cysteine tRNA synthetase. Its kinetic parameters of aminoacylation are Km=3.0 $\mu$M, kcat= 0.5 s$^{-1}$, and kcat/Km=1.67×10$^5$ M$^{-1}$sec$^{-1}$ (Hamann, C. S. & Hou, Y. M. (1995) *Biochemistry* 34, 6527–6532). These kinetic properties of the pre-annealed tRNA$^{Cys}$ are independent of the heat/cool conditions and are similar to those of the native tRNA$^{Cys}$ isolated from *E. coli* (Hou et al. (1993) *Proc. Natl. Acad. Sci. USA* 90, 6776–6780). This indicates that the pre-annealed tRNA retained the proper tRNA tertiary structure. The minor kinetic difference between the pre-annealed tRNA and the native tRNA reflects the lack of modified nucleotides in the T7 transcript. The formation of the tRNA-oligonucleotide complex therefore indicates that the oligonucleotide was able to invade the tertiary structure of the tRNA. Thus, although G15 is in the core region of tRNA$^{Cys}$, a 2'-O—Me oligonucleotide that targets G15 had access to the tRNA in the native tRNA structure. The same oligonucleotide with a deoxy backbone did not form the complex.

To establish the specificity of oligonucleotide binding, an analogous oligonucleotide (02) complementary to the sequence from U8 to A26 in yeast tRNA$^{Cys}$ was synthesized. While this oligonucleotide was capable of forming a stable complex with yeast tRNA$^{Cys}$ in a gel shift assay, it did not bind to *E. coli* tRNA$^{Cys}$. Between U8 and A26, yeast tRNA$^{Cys}$ differs from *E. coli* tRNA$^{Cys}$ in 9 nucleotides. This suggests that 9 mismatches between an oligonucleotide and its target abolished binding. Additional experiments showed that an oligonucleotide that contained three mismatches with the *E. coli* target sequence from U8 to A26 failed to bind to *E. coli* tRNA$^{Cys}$. This oligonucleotide, 03 (Table 1), differs from oligonucleotide 01 at positions 12, 15, and 21. Thus, as few as 3 mismatches between the 18-mer oligonucleotide and *E. coli* tRNA$^{Cys}$ eliminated binding.

The ability of the binding of oligonucleotide 01 to *E. coli* tRNA$^{Cys}$ to inhibit aminoacylation was then tested. Incubation of 12 $\mu$M of oligonucleotide 01 with 6 $\mu$M of the pre-annealed tRNA resulted in complete inhibition of aminoacylation. Higher ratios of the oligonucleotide to tRNA (3:1, 4:1) also elicited this complete inhibition, whereas ratios below 2:1 conferred only partial inhibition. This indicates that, within the precision of the concentrations of the oligonucleotide and tRNA$^{Cys}$, a stoichiometric amount of the oligonucleotide is sufficient to completely block aminoacylation. Even when the tRNA (6 $\mu$M) was first allowed to form a stable complex with the synthetase (12 $\mu$M), the addition of the oligonucleotide (12 $\mu$M) to the tRNA-synthetase complex abolished aminoacylation. In contrast, oligonucleotides 02 and 03 failed to inhibit aminoacylation under the same conditions. This establishes that the ability of a 2'-O—Me oligonucleotide to bind to the tRNA and to inhibit aminoacylation are well correlated.

To quantitatively assess the inhibitory effect of oligonucleotide 01, the kcat/Km parameter of aminoacylation as a function of tRNA concentration in the presence of a 2-fold molar excess of oligonucleotide 01 was determined. The kcat/Km parameter is the second-order rate constant, which determines the catalytic efficiency of aminoacylation whether the substrate concentrations are saturating or subsaturating. The effect of oligonucleotide 01 on aminoacylation can therefore be measured as the ratio of kcat/Km in the presence of oligonucleotide 01 divided by kcat/Km in the absence of oligonucleotide 01. This analysis showed that, under a range of tRNA concentrations from 0.2 $\mu$M to 16 $\mu$M, the addition of oligonucleotide 01 at a 2:1 molar ratio to tRNA$^{Cys}$ completely abolished aminoacylation.

Thus, to achieve complete inhibition of aminoacylation of tRNA$^{Cys}$, only a stoichiometric amount of the oligonucleotide is needed. It is not necessary to use a large excess of the oligonucleotide. The intracellular concentrations of tRNAs and synthetases are both in the micromolar range. This suggests that micromolar concentration of oligonucleotides inside a cell will be sufficient to achieve efficient inhibition of tRNA aminoacylation.

The minimal length of a 2'-O—Me oligonucleotide targeted to G15 of *E. coli* tRNA$^{Cys}$ required to inhibit aminoacylation was also determined. Oligonucleotides 04 to 07 that were progressively shorter in length from 14 to 5 residues were synthesized. It was found that the 5-mer (oligonucleotide 07) and 8-mer (oligonucleotide 06) did not bind to the tRNA, whereas the 10-mer (oligonucleotide 05) and 14-mer (oligonucleotide 04) did (Table 1). Each of these oligonucleotides was tested for its ability to inhibit aminoacylation at a 2:1 molar ratio to the tRNA. The kcat/Km value of aminoacylation in the presence of a particular oligonucleotide was compared to that in the absence of the oligonucleotide. Both the 10-mer and 14-mer conferred 100% inhibition of aminoacylation and thus their ability to inhibit aminoacylation is correlated with their ability to bind to the tRNA. Further, although the 8-mer did not bind to the tRNA, it was still an effective inhibitor of tRNA aminoacylation (97% inhibition). This ability of the 8-mer to almost completely inhibit aminoacylation indicates that it was able to form a complex with the tRNA but that this complex was not stable enough to survive through the gel shift assay. Because the 5-mer only conferred 20% inhibition of aminoacylation, its capacity to form a complex with the tRNA is difficult to assess. Thus, for targeting G15 of *E. coli* tRNA$^{Cys}$, the minimal length of a 2'-O—Me oligonucleotide that achieved stable binding and complete inhibition was 10.

Oligonucleotides targeted to other regions of *E. coli* tRNA$^{Cys}$ were also assessed. A 10-mer (oligonucleotide 09) complementary to the anticodon stem-loop and a 14-mer (oligonucleotide 10) complementary to the T$\psi$C stem-loop both bound to the tRNA. However, while the 10-mer completely inhibited aminoacylation, the 14-mer only showed 60% inhibition. This illustrates that the ability of an oligonucleotide to bind to the tRNA does not necessarily abolish aminoacylation. The binding of the 10-mer to the anticodon stem-loop of *E. coli* tRNA$^{Cys}$ will form a duplex with nucleotides from A37 to A46. This duplex will likely interfere with the ability of cysteine tRNA synthetase to interact with the adjacent A36 and G48 nucleotides that are critical for aminoacylation. In contrast, the T$\psi$C stem-loop of *E. coli* tRNA$^{Cys}$ does not contain major nucleotide determinants for cysteine tRNA synthetase and therefore its binding with the 14-mer has a less profound effect on aminoacylation. An 8-mer (oligonucleotide 08) which was designed to hybridize with the U73 major determinant in the acceptor stem did not bind to the tRNA and had only a 15% inhibitory effect on aminoacylation (Table 1). This is in contrast to the other 8-mer (oligonucleotide 06) which targeted G15 and almost completely inhibited aminoacylation. Thus, although G15 is in the most structured region of E. coli tRNA$^{Cys}$, and although U73 is adjacent to the single-stranded CCA end, G15 is a better target than U73 for inhibition of aminoacylation by oligonucleotides.

Accordingly, the G15:G48 tertiary base pair of E. coli tRNA$^{Cys}$ is an excellent target for binding with an antisense 2'-O— Me oligonucleotide. This base pair is also important for aminoacylation with cysteine. Compared to the U73 nucleotide and the GCA anticodon that are important for aminoacylation, the G15:G48 base pair is most accessible to targeting by antisense oligonucleotides. The accessibility of this base pair to antisense oligonucleotides indicates that it is a binding site for other small molecular weight compounds. Knowledge of the structures of these small molecular weight compounds will be useful in designing drugs that target tRNA$^{Cys}$ for aminoacylation in organisms such as E. coli and H. influenzae.

Additional experiments were carried out to further characterize oligonucleotides that target G15.

The ability of oligonucleotides to inhibit aminoacylation of E. coli tRNA$^{Cys}$ by binding specifically to the target sequence was demonstrated in experiments wherein it was shown that the oligonucleotide protected the target sequence of the tRNA from a chemical probe. oligonucleotides 01, 04, and 05 that stably bind to G15 of tRNA$^{Cys}$ and inhibit aminoacylation were tested. For this experiment, $^{32}$p labeled E. coli tRNA$^{Cys}$, either free or bound with an oligonucleotide, was treated with the chemical probe diethyl pyrocarbonate (DEPC) at a concentration that would generate statistically only one hit per tRNA molecule. DEPC attacks the N7 of A to form an aniline-sensitive adduct (Peattie, D. A., Gilbert, W. (1980) Proc. Natl. Acad. Sci. USA 77, 4679–4682). After aniline scission, the DEPC-adduct on the tRNA can be identified by electrophoresis on a denaturing gel. By this method, nucleotides in the target sequence that are hydrogen bonded in a stable structure are expected to be protected from DEPC modification whereas those in the single-stranded loops should be accessible. Protection by oligonucleotide 05, which is a 10-mer that targets A12 to A22 in the D loop, was also determined. In the native E. coli tRNA$^{Cys}$, A12–A14 and A22 were accessible to DEPC, as well as A36–A38 that are outside the target sequence. However, upon binding oligonucleotide 05 to the tRNA, A12–A14 and A22 were completely protected from DEPC whereas A36–A38 remained accessible. Additional nucleotides (such as A46) in the variable loop were also modified (the DEPC hits at the bottom of the gel when oligonucleotide 05 was bound). This indicates that the binding of oligonucleotide 05 to the tRNA denatured the tRNA structure somewhat to allow DEPC modifications of the variable loop. With oligonucleotides 01 and 04 that target longer sequences around G15, the site-specific protection of tRNA$^{Cys}$ was also evident. In all cases, protection was observed whether the tRNA-oligonucleotide complex was incubated in 10 mM MgCl$_2$ or 1 mM EDTA thus confirming that these oligonucleotides specifically bound to the target sequence and that their binding protected the target sequence from DEPC modification.

To assess the stability of the tRNA-oligonucleotide complex, the equilibrium dissociation constant for the complex formed by oligonucleotides 01, 04, or 05 was determined. For these experiments, a concentration series of E. coli tRNA$^{Cys}$ was incubated with a constant, but limiting, amount of the labeled oligonucleotide at 37° C. The distribution of free versus bound oligonucleotide was analyzed by a gel shift assay at pH 8.0. The conditions of the gel shift assay were such that a mismatched oligonucleotide and the tRNA did not form a complex by this analysis and that the detection of binding was unaffected by experimental variables such as the percentage of polyacrylamide in the gel (6% to 12%), the volume of sample loaded on the gel, or the electrophoresis time. The extent of binding was independent of incubation time (3 to 24 hrs) even at the lowest tRNA concentrations thus indicating that binding was at equilibrium. For oligonucleotide 05 (at 15 pM) it was demonstrated that the fraction of the bound oligonucleotide increased as the concentration of the tRNA (from 0.02 nM to 5 nM) increased. This relationship can be fit to a theoretical binding curve that gives a K$_d$ of about 1 nM. This K$_d$ corresponds to a binding free energy of −12.2 kcal/mol according to the equation $\Delta G° = -RT\ln(1/K_d)$, where R is the universal gas constant and T is the absolute temperature. The K$_d$ of approximately 1 nM indicates a strong association between the oligonucleotide and the tRNA and is reflective of the fact that binding of the 10 mer to the tRNA must compete against the secondary and tertiary structure that encompasses the target sequence in the D loop.

The K$_d$ of the tRNA-oligonucleotide 04 complex was determined as 0.1 nM. Thus, as the length of the oligonucleotide increased from a 10-mer to a 14-mer, the K$_d$ decreased by 10-fold, indicating enhanced affinity for the tRNA. The gain of binding free energy from 10-mer (oligonucleotide 05) to 14-mer (oligonucleotide 04) is 1.4 kcal/mol.

The rate constants for dissociation (k$_{off}$) of tRNA complexes with oligonucleotides 01, 04, and 05 were measured by competition experiments. The tRNA-$^{32}$P-labeled oligonucleotide complex was first formed by incubating 40 nM of labeled oligonucleotide with 200 nM tRNA and then was mixed with a large excess of unlabeled oligonucleotide (20 μM) that competed for the binding site. The decrease of labeled complex versus time was monitored by gel shift assays and the fraction of bound oligonucleotide was fitted to the following first order exponential decay equation.

$$\text{Fraction of bound} = (e^{k_{off} t}),$$

wherein k$_{off}$ is the dissociation rate constant.

The results showed that the dissociation rate constants for tRNA complexes with oligonucleotides 01, 04, and 05 were, respectively, $0.61 \times 10^{-4}$ S$^{-1}$, $1.3 \times 10^{-4}$ s$^{-1}$, and $3.7 \times 10^{-4}$ S$^{-1}$. From these dissociation rate constants, the half-lives of a tRNA-oligonucleotide complexes were calculated as 190 min, 92 min, and 31 min, respectively, for oligonucleotides 01, 04, and 05.

The strong affinities of these oligonucleotides to E. coli tRNA$^{Cys}$ are largely due to the 2'-O—Me modification. The deoxyribose version of oligonucleotide 01 did not even bind to tRNA$^{Cys}$ in the gel shift assay. Numerous studies have shown that the 2'-O—Me modification favors duplexes with an A-form structure (Sproat, B. S. & Lamond, A. I. (1993) in Antisense Research and Application, Crooke, S. T. & LeBleu, B., eds, pp 351–362, CRC Press, Boca Raton, Fla. Hence, 2'-O—Me oligonucleotides form highly stable hybrids with complementary RNA targets. One advantage of these stable duplexes is that inhibition of tRNA aminoacylation by the oligonucleotides of the present invention will be almost irreversible compared to the doubling time of *E. coli*. This is supported by the kinetics of dissociation mentioned above. Another advantage of the 2'-O—Me modification is that it confers inhibition of aminoacylation independent of RNase H activity. Traditional antisense inhibition is achieved by RNase H hydrolysis of the RNA strand when it is in an RNA-DNA heteroduplex (Berkower et al. (1973) *J. Biol. Chem.* 248, 5914–5921; Crouch, R. J. & Dinksen, M. L. (1982) in *Nuclease*, Linn, S. M. & Roberts, R. J. eds, p 211, Cold Spring Harbor Laboratory, Cold Spring Harbor, N.Y.; Wagner, R. W. (1994) *Nature* 372, 333–335). While 2'-O—Me oligonucleotides form more stable hybrids with RNAs, these hybrids are not substrates for RNase H (Inoue et al. (1987) *Nucleic Acid Res.* 15, 6131–6148). As a result, the uniform 2'-O—Me modification of oligonucleotides reduces or eliminates the antisense activities of these compounds. In contrast, the hybrid formed between *E. coli* tRNA$^{Cys}$ and oligonucleotides of the present invention is itself defective for aminoacylation. Therefore, RNase H should have no role in this application of antisense inhibition.

As will be obvious to one of skill in the art upon this disclosure, the methods used to identify effective oligonucleotides which inhibit aminoacylation of *E. coli* tRNA can be routinely adapted to other pathogens including, but not limited to, other bacteria, viruses, yeast, fungi and to inhibit activities of tRNAs.

Figure 2:
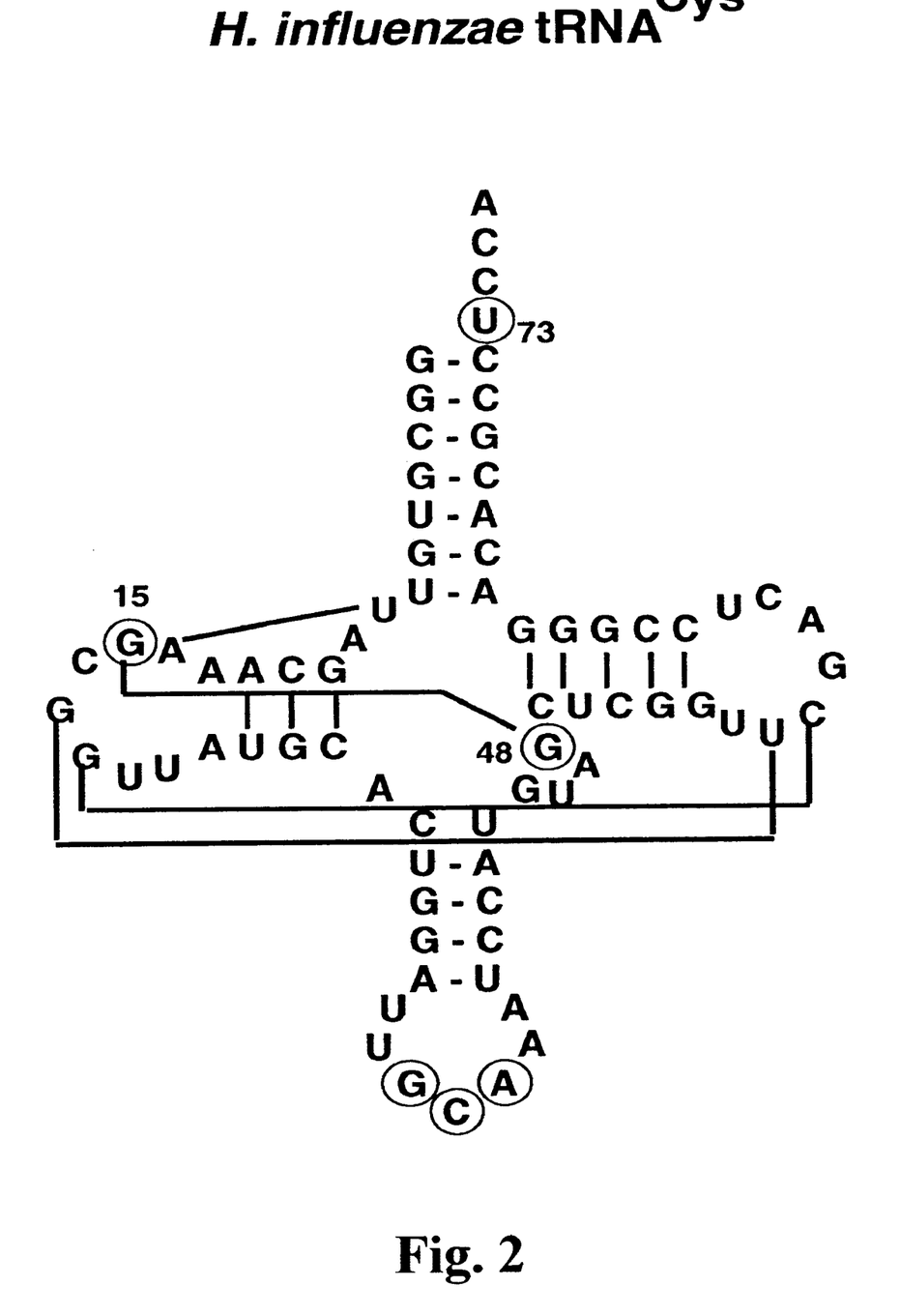

In some aspects of the invention, the oligonucleotides can be designed specifically to target sequences in the core region of a coverleaf tRNA so as to inhibit aminoacylation of the tRNA because some of the nucleotides of the core region of a cloverleaf tRNA are recognized by cognate tRNA synthetase and are important for aminoacylation of the tRNA. Particularly, 15:48 base pair and 13:22 base pair of tRNA (or 46:[13:22] base triple in some organisms' tRNA) are important for aminoacylation by cognate tRNA synthetase. For example, the G15:G48 base pair and A46:[A13:A22] base triple of *E. coli* tRNA$^{Cys}$ are also found in *H. Influenzae* tRNA$^{Cys}$ (see FIGS. 1 and 2). G15:G48 and A46:[A13:A22] are important for aminoacylation by the *H.influenzae* enzyme and *E.coli* enzyme (see Table 1 below). Specifically, the *H.influenzae* enzyme failed to efficiently aminoacylate two defective substrates for the *E.coli* enzyme, the G15:C48 and the G46:[A13:A22] variants of *E.coli* tRNA$^{Cys}$. The deficiency in $k_{cat}$ and $K_m$ of aminoacylation with the G15:C48 variant and that with the G46:[A13:A22] variant were quantitatively similar to those of the *E. coli* enzyme. Thus, the sequence conservation of G15:G48 and A13, A22 and A46 between *E.coli* and *H.influenzae* tRNAs has functional significance. Further, the structural coupling between G15:G48 and the A46:[A13:A22] triple in *E.coli* tRNA$^{Cys}$ is preserved in the *H.influenzae* tRNA as well. Specifically, while substitution of A13 with U13 was functional, and while substitution of U21 with A21 was functional, the double mutant containing both the A13U and U21A substitutions was defective in *E.coli* tRNA$^{Cys}$. The defect of the double mutant was manifested in two features. One was the loss of the chemical signature of G15:G48 in the tRNA. The other was a decrease in the $k_{cat}$ and $K_m$ of aminoacylation by two orders of magnitude. The two features displayed by the double mutant were tightly coupled and this coupling is important for aminoacylation by the *E.coil* enzyme. Table 1 shows that the *H.influenzae* enzyme also emphasized the coupling as it failed to aminoacylate the double mutant containing the A13U and U21A mutations. The decrease in $k_{cat}$ and $K_m$ of aminoacylation with the double mutant is quantitatively similar to that for the *E.coli* enzyme.

It is also shown by this invention, the catalytic properties of aminoacylation of the *H.influenzae* enzyme are strikingly similar to those of the *E.coli* enzyme (see Table 1 below). First, the *H.influenzae* enzyme efficiently aminoacylated the T7 transcript of *H.influenzae* tRNA$^{Cys}$ with a $k_{cat}/K_m$. (1.8× $10^5$ M$^{-1}$ s$^{-1}$) that is comparable to that of the *E.coli* enzyme with the T7 transcript of *E. coli* tRNA$^{Cys}$ (2.1×$10^5$ M$^{-1}$ s$^{-1}$). The similarity in the $k_{cat}/K_m$ values is a result of similar $k_{cat}$ and $k_m$ for each tRNA by its homologous synthetases. The *E.coli* tRNA has a $k_{cat}$ of 0.5 s$^{-1}$ and a $K_m$ of 2.38 $\mu$M The *H.influenzae* tRNA has a $k_{cat}$ of 0.52 s$^{-1}$ and a $K_m$ of 2.89 $\mu$M. Second, the *H.influenzae* enzyme and the *E.coli* enzyme were capable of cross-aminoacylation of each other's tRNA. The $k_{cat}/K_m$ of aminoacylation of the *Ecoli* tRNA by the *H.influenzae* enzyme is 1.4 relative to that of the homologous *H.influenzae* tRNA. Similarly, the $k_{cat}/K_m$, of aminoacylation of the *H.influenzae* tRNA by the *E.coli* enzyme is 0.8 relative to that of the homologous *Ecoli* tRNA. The $k_{cat}/K_m$ value of the *H.influenzae* enzyme with its own T7 transcript and the $k_{cat}/K_m$ of the enzyme with the T7 transcript of *E.coli* tRNA are similar to each other and to those of the *E.coli*. Despite differences in their primary structures, the two tRNAs share common structural motifs that are important for aminoacylation by the *H.influenzae* and *E.coli* enzymes.

Thus, drugs that target the G15:G48 base pair and A46:[A13:A22] base triple of *E. coli* tRNA$^{Cys}$ are also expected to target G15:G48 base pair and A46:[A13:A22] base triple of *H. Influenzae* tRNA$^{Cys}$.

TABLE 1

Kinetic parameters of aminoacylation of tRNA$^{Cys}$, of *H. influenzae* and *E. coli* by their respective cysteine-tRNA synthetases

|  | [1]$K_{cat}/K_m$ (M$^{-1}$ s$^{-1}$) | Relative |
|---|---|---|
| *Haemophilus influenzae* cysteine-tRNA synthetase | | |
| *H. influenzae* tRNA$^{Cys}$ | 1.8 × $10^5$ | 1.00 |
| *E. coli* tRNA$^{Cys}$ | 2.6 × $10^5$ | 1.4 |
| The G15:C48 variant of *E. coli* tRNA$^{Cys}$ | 4.1 × $10^3$ | 0.023 |
| The A 13: A22:G46 variant of *E. coli* tRNA$^{Cys}$ | 4.4 × $10^3$ | 0.024 |
| The A13U and U21A variant of *E. coli* tRNA$^{Cys}$ | 2.2 × $10^3$ | 0.012 |
| *B. subtilis* tRNA$^{Cys}$ | 2.5 × $10^5$ | 1.4 |
| *Escherichia coli* cysteine-tRNA synthetase | | |
| *H. influenzae* tRNA$^{Cys}$ | 1.7 × $10^5$ | 0.81 |
| *E. coli* tRNA$^{Cys}$ | 2.1 × $10^5$ | 1.00 |
| The G15:C48 variant of *E. coli* tRNA$^{Cys}$ | 7.8 × $10^3$ | 0.037 |
| The A13:A22:G46 variant of *E. coli* tRNA$^{Cys}$ | 4.6 × $10^3$ | 0.027 |
| The A13U and U21A variant of *E. coli* tRNA$^{Cys}$ | 2.3 × $10^3$ | 0.013 |
| *B. subtilis* tRNA$^{Cys}$ | 3.4 × $10^5$ | 1.6 |

[1]The $k_{cat}/K_m$ values were determined by individually measuring $k_{cat}$ and $K_m$ through the Michaeilis-Menten equation and were an average of at least three determinations.

Indeed, the target sequence for the 10 mer 2'-O—Me oligonucleotide for G15:G48 of *E. coli* is also found in the *H. influenzae* tRNA$^{Cys}$ thus indicating that the 10 mer 2'-O—Me oligonucleotide will also bind to *H. influenzae* tRNA$^{Cys}$ and inhibit aminoacylation. Accordingly, inhibitors that bind to G15:G48 are expected to inhibit protein synthesis of both *E. coli* and *H. influenzae*, leading to cell death. Because *E. coli* and *H. influenzae* are important causes of community- and hospital-acquired infections, the ability to inhibit their cell growth via sequence specific antisense oligonucleotides or derivatives thereof will have long-reaching effects on improving public health The E.coli and H.influenzae enzymes can also aminoacylate the B.subtilis tRNA$^{Cys}$. The $k_{cat}$ and $K_m$ value of the B.subtilis tRNA for the E.coli enzyme relative to that of the E.coli tRNA is 1.6 (Table 1). Similarly, the $k_{cat}$ and $K_m$ value of the B. subtilis tRNA for the H.influenzae enzyme relative to that of the H.influenzae tRNA is 1.4. The B.subtilis tRNA shares the same D3V4 configuration (3 bp in the D stem and 4 nt in the V loop) as the E.coli and H.influenzae tRNAs (Table 2). However, the B.subtilis tRNA differs from the E.coli and H.influenzae tRNAs by having G15:C48 (instead of G15:G48), U46 (instead of A46) and A21 (instead of U21) in the tRNA core. The efficient activity of this tRNA with both the E. coli and H.influenzae enzymes provides an example of a tRNA core featuring G15:C48 that can be efficiently recognized by these two enzymes.

Thus, it is shown in the present invention that the B.subtilis tRNA$^{Cys}$ is an efficient substrate for both the E. coli and H. influenzae enzymes. The efficient aminoacylation of this tRNA by the E. coli and H.influenzae enzymes is unexpected. The B.subtilis tRNA is a representative of the major subclass of eubacterial tRNAs. Thus, by efficient aminoacylation of the B.subtilis tRNA, the effect of G15:C48 in this tRNA is compensated for by other features in the core, such as lack of the 46:[13:22] base triple. The members of the other subclass of eubacterial tRNAs featuring G15:C48 and G 13:A22 in the D3V4 configuration are also efficiently aminoacylated by the E.coli enzyme (data not presented here). Thus, while G15:G48 in the tRNA core is important for aminoacylation for the E.coli and H.influenzae enzymes, there is a certain sequence context in which G15:C48 can function.

In addition, using the methods disclosed herein, oligonucleotides can be designed to target the 3' end of human tRNA$^{Lys}$, which hybridizes to the HIV genomic RNA and functions as a primer for reverse transcription by the viral polymerase. In this embodiment, 2'-O-alkyl oligonucleotides are synthesized that are identical in sequence to the 3' end of tRNA$^{Lys}$ and used as competitive inhibitors of HIV reverse transcriptase. Because these oligonucleotides can be administered at a much higher concentration than the normal concentration of tRNA$^{Lys}$, and because these oligonucleotides afford a more stable complex with the HIV RNA than tRNA$^{Lys}$, these oligonucleotides will effectively compete out the tRNA for binding to the viral genome, thereby inhibiting stable infection of cells by HIV. As will be obvious to those of skill in the art, this method is also applicable to other retroviruses. Further, oligonucleotides of the present invention can be targeted to human tRNAs as a means for arresting the growth of malignant cells using a delivery system which is selective for tumor cells. Accordingly, oligonucleotides of the present invention are also useful as anticancer agents.

The following nonlimiting examples are provided to further illustrate the present invention.

EXAMPLES

Example 1

Synthesis and Radiolabeling of 2'-O—Me Oligonucleotides

Synthesis of oligonucleotides with 2'-O—Me phosphoramidites (Glen Research Corp., Sterling, Va.) was performed on a Pharmacia automated synthesizer (Piscataway, N.J.). Each oligonucleotide was synthesized with an acridine-derivatized controlled-pore glass (CPG) support so that the 3' end of the oligonucleotide would contain an acridine group. Oligonucleotides were purified by HPLC on a reverse-phase column with an acetonitrile gradient (usually 0–45%) in 100 mM triethylamine acetate (pH 7.5) buffer in accordance with the procedure disclosed by Gamper et al., (1993) Nucleic Acids Res. 21, 145–150. All oligonucleotides were at least 95% pure when evaluated by electrophoresis on a 20% denaturing polyacrylamide gel, followed by silver staining for visualization.

Oligonucleotides were labeled at the 5'-end by T4 polynucleotide kinase with $\gamma$-$^{32}$P-ATP (New England Nuclear, >3000 Ci/mmol). The labeled oligonucleotides were separated from free ATP by electrophoresis in a 20% polyacrylamide/7 M urea gel and were eluted from the gel in 0.125 M ammonium acetate, 0.125 mM EDTA (ethylene diamine tetra-acetic acid), and 0.025% SDS (sodium dodecyl sulfate). The eluted oligonucleotides were precipitated by ethanol with carrier and resuspended. Specific activities of the labeled oligonucleotides were 3600–4200 cpm/fmol.

Example 2

Preparation of tRNA Transcripts and Aminoacylation Assays

All tRNA transcripts were made by T7 RNA polymerase from tRNA genes that were constructed in plasmid pTFMa as described by Hou et al. (1993) Proc. Natl. Acad. Sci. USA 90, 6776–6780. Transcription was performed for 4 hours at 37° C. in a reaction that contained 40 mM Tris-HCl, pH 8.0, 24 mM MgCl$_2$, 1 mM spermidine, 5 mM dithiothreitol, 0.01% triton X-100, 0.24 U/mL RNasin, 4 mM NTP, and 16 mM GMP. Full-length transcripts were purified by electrophoresis (12% polyacrylamide/7 M urea) and ethanol precipitated. Concentrations of tRNAs were determined by absorption at 260 nm (1 OD260=0.04 mg/mL RNA).

Aminoacylation of tRNAs with cysteine was assayed at 37° C. in accordance with procedures described by Hou et al. (1993) Proc. Natl. Acad. Sci. USA 90, 6776–6780 and Hamann, C. S. & Hou, Y. M. (1995) Biochemistry 34, 6527–6532). To determine the effect of oligonucleotides on tRNA aminoacylation, tRNAs were pre-annealed (80° C., 2 minutes, 37° C., 30 minutes in 10 mM Tris-HCl, pH 8.0, 1 mM EDTA, 20 mM MgCl$_2$) and then incubated with an oligonucleotide at 37° C. for 15 minutes prior to the addition of the assay buffer and the enzyme (1 nM). Aminoacylation was monitored for 10 minutes at 37° C. while aliquots at different time points were removed and precipitated by 5% trichloroacetic acid on filter pads. The filter pads were washed with ethanol and ether, dried, and counted in scintillation fluor. For determination of kcat/Km of aminoacylation, tRNA concentrations ranged from 0.2 $\mu$M to 16 $\mu$M.

Example 3

Gel Shift Assays

Oligonucleotides labeled at the 5'-end were used for the tRNA gel shift assay as described by Pyle et al. (1990) Proc. Natl. Acad. Sci. USA 87, 8187–8191; Bhattacharyya et al. (1990) Nature 343, 484–487; Lima et al. (1992) Biochemistry 31, 12055–12061. Assays were performed by incubating a pre-annealed tRNA transcript (2 $\mu$M) with a labeled oligonucleotide (1,000 cpm, 4 $\mu$M) in 24 $\mu$L of annealing buffer (10 mM Tris-HCl, pH 8.0, 1 mM EDTA, and 20 mM MgCl$_2$) for 30 minutes at 37° C. A 10× loading buffer containing 40% glycerol and 0.5% each xylene cyanol and bromophenol blue was added, and 5 μL of the sample was loaded onto a 12% polyacrylamide gel (43 cm×30 cm×0.4 mm, 89 mM Tris-HCl, pH 8.3, 89 mM borate, 2 mM EDTA, and 5 mM MgCl$_2$). The complex of tRNA and oligonucleotide was separated from free species by non-denaturing electrophoresis in gel buffer at room temperature and at 750 volts until bromophenol blue reached the bottom. The gel was analyzed by autoradiography to determine the fraction of bound oligonucleotide.

Example 4

Determination of the Hybridization Rates and Equilibrium Dissociation Constants of tRNA-Oligonucleotide Complexes To measure the dissociation rate of a tRNA-oligonucleotide complex, a $^{32}$P-labeled oligonucleotide (40 nM) and pre-annealed tRNA$^{Cys}$ (200 nM) were incubated together in the annealing buffer for 1 hour at 37° C., then unlabeled oligonucleotide (20 μM) was added so that the final concentration of the oligonucleotide was 500-fold greater than that of the labeled oligonucleotide. A reaction of 50 μL was incubated at 37° C. and aliquots of 5 μL were removed at specific time intervals and immediately snap-frozen on dry ice. Reactions were individually thawed and loaded onto a non-denaturing gel as described above. The relative distribution of label between the free and bound oligonucleotide was quantified by a phosphorimager (Molecular Dynamics, Sunnyvale, Calif.).

To determine the equilibrium constant of a tRNA-oligonucleotide complex, 15 pM of a 5'-labeled oligonucleotide (1000 cpm) was incubated with a concentration series of pre-annealed E. coli tRNA$^{Cys}$ (20 pM to 5 nM) in annealing buffer at 37° C. for 24 hours. After addition of the 10× loading buffer, reactions were analyzed by non-denaturing gel electrophoresis as described above.

Example 5

Protection of tRNA$^{Cys}$ from Chemical Modification by Oligonucleotides

E. coli tRNA$^{Cys}$ transcript was labeled at the 3' end by T4 RNA ligase and [5'-$^{32}$p]pCp (New England Nuclear, 3000 Ci/mmol). Approximately 1 pmole of the pre-annealed labeled tRNA was incubated with 140 pmoles of an oligonucleotide in the annealing buffer for 30 minutes at 37° C. The complex of tRNA-oligonucleotide was treated with diethylpyrocarbonate (DEPC) in accordance with procedures described by Peattie, D. A., Gilbert, W. (1980) Proc. Natl. Acad. Sci. USA 77, 4679–4682 and Ehresmann et al. (1987) Nucleic Acids Res. 21, 413–417. Aniline induced cleavage sites were detected by electrophoresis of the RNA fragments on a 12% denaturing polyacrylamide gel.

Example 6

Nitrocellulose Filter Binding Assay

The T7 transcript of E. coli tRNA$^{Cys}$ was labeled at the 5' end by T4 polynucleotide kinase and θ-$^{32}$P-ATP and purified by denaturing gel electrophoresis. The labeled tRNA (2 nM, 5000 cpm) was pre-annealed and added to a binding mixture of 100 μL that contained 60 mM sodium acetate, pH 5.0, 10 mM MgCl$_2$ and 50 mM NaCl with varying amounts of cysteine tRNA synthetase (0 to 320 nM). After incubation at room temperature for 15 seconds, the binding mixture was passed through a nitrocellulose filter paper (25 mm, Schleicher & Schuell, Keene, N.H.) that had been previously washed with 0.4 M KOH for 40 minutes, rinsed with water twice, and equilibrated in wash buffer (60 mM sodium acetate, pH 5.0, 5 mM MgCl$_2$). The filter paper was washed with 2 mL of wash buffer, air-dried, and counted in 10 mL of scintillation fluor. The concentration of the enzyme at which 50% binding was observed is the apparent K$_d$.

Example 7

Chemical Modification of tRNAs

Procedures for the DMS modification of N7 of G15 have been described (Hamann, et al., 1997, Biochemistry, 36,7967–7972; Hamann, et al., 1997, Bioorg. Med. Chem., 5, 1011–1019.). The site of modification was detected by aniline scission (Ehresmann, et al., 1987, Nucleic Acids Res., 15,9109–9128). An N7 of G15 accessible to DMS is the chemical signature of E.coli tRNA$^{Cys}$, and it indicates protrusion of the purine ring of G15 from that of A14 (Hou, et al., 1993, Proc. Natl. Acad. Sci. USA, 90:6776–6780).

Example 8

Cloning and Expression of the Gene for H.influenzae Cysteine-tRNA Synthetase

Two primers for amplification of the gene for H.influenzae cysteine-tRNA synthetase were designed from H.influenzae genomic DNA (ATCC51907) (Fleischmann, et al, 1995, Science, 2691, 496–512) by PCR. The forward primer (5'-GCG GTC GAC ATG CTA AAA ATT TTC AAT ACC TTA A-3') (SEQ ID NO: 13) corresponds to the N-terminus of the gene, while the reverse primer (5'-CGC ACT AGT CTA TTG CTT ACG CCA AGT TGT CCC A-3') (SEQ ID NO: 14) corresponds to the C-terminus of the gene. The PCR product was cloned into the pTZ19R vector (Bio-Rad) and errors that arose during the PCR reaction were corrected by site-directed mutagenesis. The correct gene was excised by digestion with SalI and SpeI and subcloned into the corresponding sites of the pKS583 expression vector (Shiba, et al., 1997, 1 Biol. Chem., 272, 22809–22816) to produce the construct pM392. In pM392, the gene for H.influenzae cysteine-tRNA synthetase is fused to a sequence at the 5'-end so that expression of the gene will result in an N-terminal (His)$_6$ tag (N-MRGSHHHHHHSS-GWVD) (SEQ ID NO: 15). For protein expression, E.coli BL21 (DE3) (Studier, et al., 1990, Methods Enzymol., 185, 60–89) was transformed by pM392, and transformed cells were grown in LB broth with 100 μg/ml ampicillin and induced at an OD$_{600}$ of 0.5 with 1 mM IPTG for 4 h. The overexpressed H.influenzae cysteine-tRNA synthetase was purified using the B-PER 6×His Protein Purification kit as described by the manufacturer (Pierce Inc.).

What is claimed is:

1. A composition which inhibits activities of a tRNA comprising an oligonucleotide which is fully complementary to a sequence set forth in SEQ ID NO:1, 2, 4, 5, 6, 9 or 10.

2. The composition of claim 1 wherein the oligonucleotide is chemically modified.

3. The composition of claim 2 wherein the oligonucleotide comprises a 2'-O-alkyl oligonucleotide.

4. The composition of claim 3 wherein the sequence is SEQ ID NO:1.

5. The composition of claim 3 wherein the sequence is SEQ ID NO:2.

6. The composition of claim 3 wherein the sequence is SEQ ID NO:4.

7. The composition of claim 3 wherein the sequence is SEQ ID NO:5.

8. The composition of claim 3 wherein the sequence is SEQ ID NO:6.

9. The composition of claim 3 wherein the sequence is SEQ ID NO:9.

10. The composition of claim 3 wherein the sequence is SEQ ID NO:10.

11. The composition of claim 1 wherein the oligonucleotide is targeted to the region of a cloverleaf structure of a tRNA having a tertiary structure.

12. The composition of claim 1 wherein the inhibited activities of the tRNA include the ability to be aminoacylated by a cognate aminoacyl tRNA synthetase.

13. The composition of claim 1 wherein the inhibited activities of the tRNA includes peptide bond formation in protein synthesis.

14. A composition comprising an oligonucleotide, wherein the oligonucleotide is fully complementary to a target selected from the group consisting of:

(a) a sequence consisting of nucleotides set forth in SEQ ID NO.:1;

(b) a sequence consisting of nucleotides set forth in SEQ ID NO.:2;

(c) a sequence consisting of nucleotides set forth in SEQ ID NO.:4;

(d) a sequence consisting of nucleotides set forth in SEQ ID NO.:5;

(e) a sequence consisting of nucleotides set forth in SEQ ID NO.:6;

(f) a sequence consisting of nucleotides set forth in SEQ ID NO.:9; and (g) a sequence consisting of nucleotides set forth in SEQ ID NO.:10;

wherein the oligonucleotide inhibits the ability of a tRNA to be aminoacylated by a cognate tRNA synthetase in a cell.

15. A 2'-O-alkyl oligonucleotide targeted to a region consisting of or adjacent to one or more cognate tRNA synthetase recognition nucleotides of a cloverleaf structure of a tRNA$^{Cys}$ of E. coli or H. influenzae, wherein the oligonucleotide is fully complementary to a sequence set forth in SEQ ID NO: 4.

16. A 2'-O-alkyl oligonucleotide targeted to a region consisting of or adjacent to one or more cognate tRNA synthetase recognition nucleotides of a cloverleaf structure of a tRNA$^{Cys}$ of E. coli or H. influenzae, wherein the oligonucleotide is fully complementary to a sequence set forth in SEQ ID NO: 5.

17. A 2'-O-alkyl oligonucleotide targeted to a region consisting of or adjacent to one or more cognate tRNA synthetase recognition nucleotides of a cloverleaf structure of a tRNA$^{Cys}$ of E. coli or H. influenzae, wherein the oligonucleotide is fully complementary to a sequence set forth in SEQ ID NO: 6.

18. A method of inhibiting activities of a tRNA of a bacterium comprising contacting the bacterium with an oligonucleotide which is fully complementary to a sequence set forth in SEQ ID NO: 1, 2, 4, 5, 6, 9 or 10 that is targeted to a region of a cloverleaf structure of the tRNA such that activities of the tRNA are inhibited wherein the bacterium is E. coli or Hinfluenzae.

19. The method of claim 18 wherein the oligonucleotide is chemically modified.

20. The method of claim 19 wherein the oligonucleotide is a 2'-O-alkyl oligonucleotide.

21. The method of claim 18 wherein the oligonucleotide is targeted to a region of the cloverleaf structure of a tRNA having a tertiary structure.

22. The method of claim 19 wherein the activities of the tRNA comprise the ability to be aminoacylated by a cognate aminoacyl tRNA synthetase.

23. The method of claim 18 wherein the activity of the tRNA comprises peptide bond formation in protein synthesis.

24. A method of inhibiting aminoacylation of a cloverleaf structure of a tRNA in a bacterial cell comprising contacting the bacterial cell with 2'-O-alkyl oligonucleotide which is fully complementary to a sequence set forth in SEQ ID NO1, SEQ ID NO:2, SEQ ID NO: 4, SEQ ID NO: 5, SEQ ID NO: 6, SEQ ID NO: 9, or SEQ ID NO 10 such that aminoacylation of the cloverleaf structure of the tRNA is inhibited, wherein the bacterial cell is *E. coli* or *H. influenzae*.

* * * * *